US010143587B2

(12) United States Patent
Lucke

(10) Patent No.: US 10,143,587 B2
(45) Date of Patent: Dec. 4, 2018

(54) OPHTHALMIC SURGICAL DEVICE

(71) Applicant: EOS GMBH, Eschweiler (DE)

(72) Inventor: Klaus Lucke, Bremen (DE)

(73) Assignee: EOS GMBH, Eschweiler (DE)

(*) Notice: Subject to any disclaimer, the term of this patent is extended or adjusted under 35 U.S.C. 154(b) by 401 days.

(21) Appl. No.: 14/761,258

(22) PCT Filed: Jan. 2, 2014

(86) PCT No.: PCT/EP2014/050006
§ 371 (c)(1),
(2) Date: Jul. 15, 2015

(87) PCT Pub. No.: WO2014/111270
PCT Pub. Date: Jul. 24, 2014

(65) Prior Publication Data
US 2015/0359670 A1 Dec. 17, 2015

(30) Foreign Application Priority Data

Jan. 15, 2013 (EP) .................................. 13151278

(51) Int. Cl.
*A61F 9/00* (2006.01)
*A61F 2/16* (2006.01)
(Continued)

(52) U.S. Cl.
CPC .......... *A61F 9/00736* (2013.01); *A61B 34/25* (2016.02); *A61B 50/15* (2016.02);
(Continued)

(58) Field of Classification Search
CPC ........ A61B 2034/252; A61B 2034/254; A61B 2034/255; A61B 2034/256;
(Continued)

(56) References Cited

U.S. PATENT DOCUMENTS 6,158,437 A 12/2000 Vagley
6,312,258 B1* 11/2001 Ashman .................. A61C 8/00
206/369

(Continued)

FOREIGN PATENT DOCUMENTS

DE 102009005642 A1 4/2010
EP 1 428 541 B1 6/2006

OTHER PUBLICATIONS

PCT/EP2014/050006, Apr. 1, 2014, International Search Report and Written Opinion.

*Primary Examiner* — Victor Nguyen
(74) *Attorney, Agent, or Firm* — Workman Nydegger

(57) ABSTRACT

The invention relates to a device (1) for use in surgery to which a surgical implement is connectable in order to conduct surgery on a patient, wherein input means (7) for controlling operating parameters and display means (8) for indicating the operating parameters are provided, wherein the device (1) comprises a first display (9) which is essentially horizontal during operation and a second display (10) which runs obliquely upwards at an installation angle (A), wherein the device (1) exhibits position detection means (18) for detecting contactlessly communicating surgical implements (2, 14, 15) deposited on the first display (9) with regard to their positions on the first display (9).

11 Claims, 2 Drawing Sheets

(51) Int. Cl.
| | |
|---|---|
| *A61F 9/007* | (2006.01) |
| *A61B 50/26* | (2016.01) |
| *G06F 3/14* | (2006.01) |
| *A61B 50/15* | (2016.01) |
| *A61B 50/20* | (2016.01) |
| *A61B 50/24* | (2016.01) |
| *A61B 50/33* | (2016.01) |
| *A61B 90/90* | (2016.01) |
| *A61B 90/98* | (2016.01) |
| *A61B 17/00* | (2006.01) |
| *A61B 90/00* | (2016.01) |
| *A61B 34/00* | (2016.01) |

(52) U.S. Cl.
CPC .............. *A61B 50/20* (2016.02); *A61B 50/24* (2016.02); *A61B 50/26* (2016.02); *A61B 50/33* (2016.02); *A61B 90/90* (2016.02); *A61B 90/98* (2016.02); *A61F 9/00745* (2013.01); *G06F 3/1423* (2013.01); *A61B 2017/00199* (2013.01); *A61B 2034/252* (2016.02); *A61B 2034/254* (2016.02); *A61B 2090/0804* (2016.02)

(58) Field of Classification Search
CPC ... A61B 2034/257; A61B 34/25; A61B 50/15; A61B 19/56; A61B 2019/562; A61F 9/00736; A61F 2/16; A61F 9/00
USPC ........................................................ 606/107
See application file for complete search history.

(56) References Cited

U.S. PATENT DOCUMENTS

| | | |
|---|---|---|
| 2004/0186683 A1 | 9/2004 | Farber et al. |
| 2006/0142739 A1 | 6/2006 | DiSilestro et al. |
| 2010/0174415 A1 | 7/2010 | Humayun et al. |
| 2011/0190690 A1* | 8/2011 | Humayun ........... A61F 9/00736 604/22 |

* cited by examiner

OPHTHALMIC SURGICAL DEVICE

The invention relates to a device for use in surgery to which a surgical implement is connectable in order to conduct surgery on a patient, wherein input means for controlling operating parameters and display means for indicating the operating parameters are provided.

Document EP 1 428 541 B1 discloses such a device by means of which a new lens can be inserted into the eye of a patient during cataract surgery. During the surgery, at first a cut is placed on the eye by the surgeon with a surgical handpiece, via which the old lens, which has been divided into small pieces, is removed and, subsequently, the new lens is introduced into the eye. In order to facilitate the removal of the small pieces of the old lens and to prevent the volume in the eye originally occupied by the old lens from collapsing during the surgery, the fluid must be delivered from the surgical handpiece into the eye on which surgery has been performed at an irrigation pressure. An irrigation pressure which is too high would permanently damage the eye, and at an irrigation pressure which is too low the eye is in danger of collapsing, for which reason the surgeon has to be able to adjust the appropriate irrigation pressure. This and further operating parameters must be set on the device by the surgeon and must be adjusted continuously during the surgery.

Furthermore, it is increasingly important for surgical procedures to record every action of the surgeon or the surgical nurse in order to ensure a high quality standard for operations and to have sufficient evidence for possible lawsuits. In this connection, devices from other fields are known which compile a surgical protocol in which the operating parameters set in each case are recorded and saved during the surgery.

The known device has been shown to have the disadvantage that the device and, in this connection, in particular the input means of the device get soiled heavily during the surgery and can be cleaned only with difficulty. Furthermore, the known device has turned out to be disadvantageous in that, in individual cases, the surgical protocol has not been sufficient for retracing the sequence of the operation reliably and completely.

The invention is based on the object of providing a device for use in eye surgery with which the previously indicated disadvantages are avoided.

According to the invention, this problem is solved in that the device comprises a first display which is essentially horizontal during operation and a second display which runs obliquely upwards at an installation angle, wherein the device exhibits position detection means for detecting contactlessly communicating surgical implements deposited on the first display with regard to their positions on the first display.

As a result, the advantage is obtained that the device detects the surgical implements deposited on the first display, whereby a plurality of features are enabled for improving the surgical protocol and for cleaning the device in a better way. For example, it has turned out to be advantageous to indicate on the first display the surgical implements required for the respective type of eye surgery in a true-to-life manner of illustration and to give clearance for the surgery only if either all the required surgical implements are in their proper place on the first display or if a query information to the surgeon or the surgical nurse has been answered.

It is also particularly advantageous to record in the surgical protocol when which surgical implement was removed from the first display and was put back down. As a result, it is not only possible to retrace the surgery afterwards precisely on the basis of the surgical protocol, but also certain operating parameters can be set automatically by the device control when a particular surgical implement has been taken from the first display of the device for the surgical procedure. The display information indicated on the first display and/or the second display can also be modified for the surgeon depending on the surgical implement just in use.

Due to the smooth surfaces of the first display and the second display, which, apart from a foot switch, constitute all input means and display means of the device, the device can be cleaned particularly well. This is particularly important and advantageous for a device to be used in an operating room.

Further advantageous embodiments of the device according to the invention are explained in further detail below on the basis of the figures.

Figure 1:
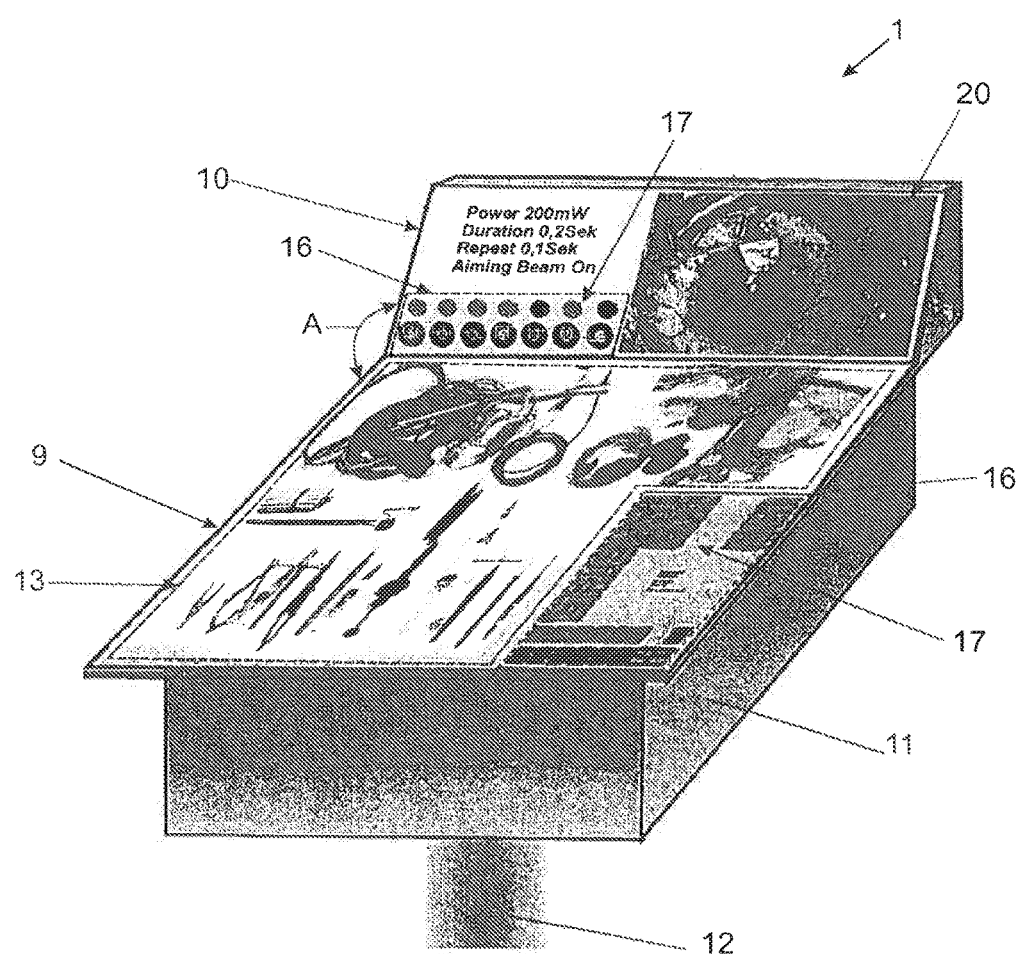
FIG. 1 shows a device for use in eye surgery.
Figure 2:
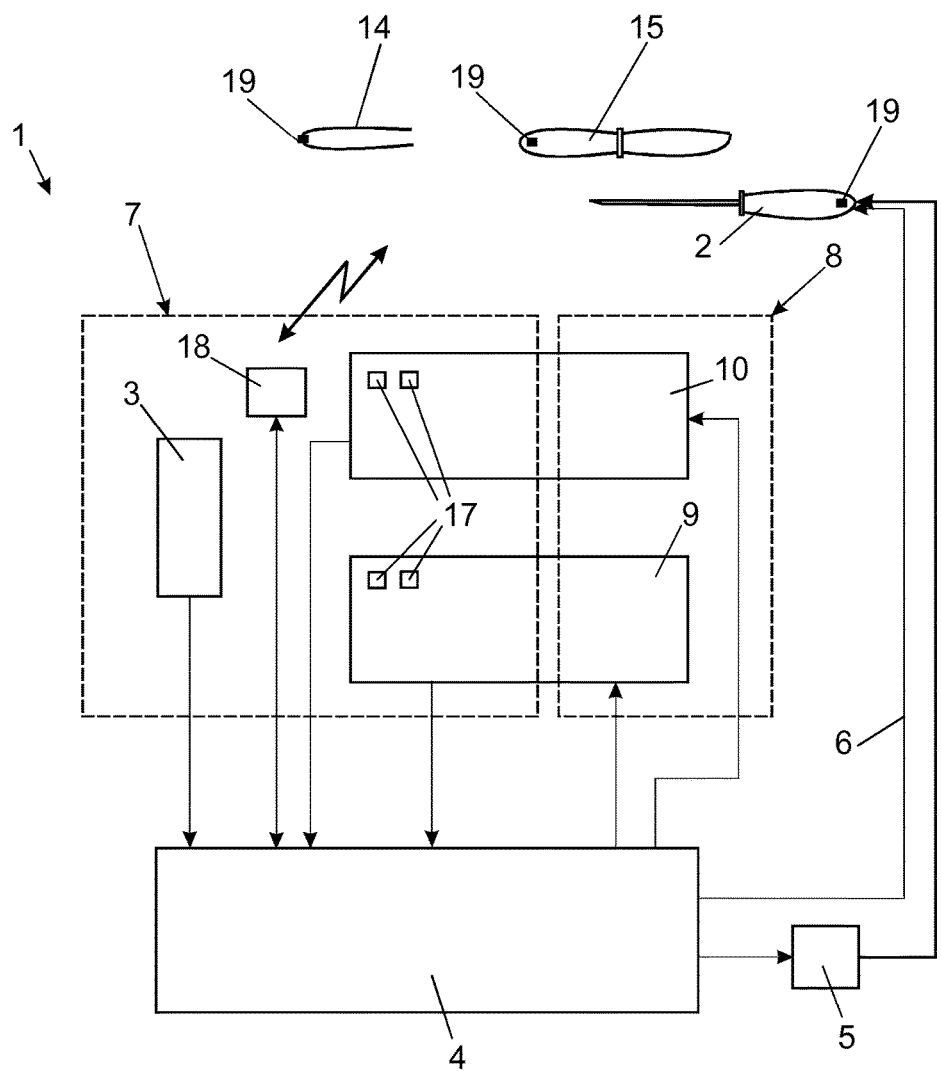
FIG. 2 shows a block diagram of the basic functional blocks of the device according to FIG. 1.

FIG. 1 shows a device 1 for use in eye surgery to which a surgical handpiece 2 as illustrated in the block diagram of FIG. 2 is connectable. Using the device 1, a new lens can be inserted into the eye of a patient. During the surgery, at first a cut is placed on the eye by the surgeon and, subsequently, the eye is operated on with the surgical handpiece 2.

The surgical handpiece 2 fulfills three functions during the surgery. At an irrigation opening, fluid or rinsing fluid, respectively, for rinsing the eye is delivered from the surgical handpiece 2 into the eye at an irrigation pressure predetermined by the surgeon with a foot switch 3. A knife provided in the surgical handpiece 2 and driven by a piezo divides the old lens into small pieces which are sucked in together with the rinsing fluid via an aspiration opening of the surgical handpiece 2 and are collected in a cartridge of the device 1.

By means of the foot switch 3, the surgeon is able to predetermine both the momentarily desired irrigation pressure and the momentarily desired negative pressure for suction at the aspiration opening of the surgical handpiece 2. Furthermore, the device 1 comprises a device control 4 as illustrated in FIG. 2 which is implemented by a computer including a computer program of the device 1 and controls both the irrigation pressure predetermined by the foot switch 3 at the irrigation opening and the predetermined negative pressure at the aspiration opening. This is effected by pressure means 5 which are implemented by a pillar of the rinsing liquid which is adjustable in its height or by pressurizing means. Via a control line 6, the device control 4 actuates also the piezo of the knife in the surgical handpiece 2.

In addition to the foot switch 3, the device 1 now comprises further input means 7 for controlling operating parameters and display means 8 for indicating the operating parameters and other information of interest to the surgeon. Said input means 7 and display means 8 are formed by a first display 9 which is essentially horizontal and a second display 10 which, seen from the surgeon's point of view, is located behind it and runs obliquely upwards at an installation angle A. According to said exemplary embodiment, the first display 9 is located on a casing 11 which is placed on the floor of the operating room by means of a device base 12.

On the first display 9, true-to-life depictions of the individual surgical implements to be used for the respective eye surgery are indicated. Depending on the type of eye surgery, different surgical implements are required during the surgery which have to be prepared by the surgical nurse prior to the surgical procedure. In FIG. 1, a plurality of such surgical implements are illustrated in a display area 13, with forceps 14, a knife 15 and the surgical handpiece 2 being exemplified in FIG. 2.

The first display 9 and the second display 10 constitute, in addition to the foot switch 3, also the input means 7, for which purpose keys 17 implemented as a touchscreen are illustrated in a further display area 16. By means of the keys 17, the respective type of eye surgery can be chosen and further entries such as, for example, the setting of operating parameters or the entry of patient identifications can be made.

The device 1 now comprises position detection means 18 for detecting contactlessly communicating surgical implements deposited on the first display 9. The position detection means 18 are formed by an RFID reader in the HF or UHF frequency range as well as several antennas arranged so as to be distributed in the first display 9 or in the casing 11, respectively. At this, the position and the transmitting power of those antennas are chosen such that the position of a surgical implement provided with an RFID label 19 (sticker containing a passive and contactlessly readable RFID tag) can be detected. For example, one antenna at a time in cyclic succession would be able to release transmitting power in a localized way, whereupon the serial numbers of RFID labels 19 located in said localized transmission range on the first display 9 could be read out. After a passage through all antennas, the serial numbers read out from the RFID labels 10 could be compared to a stored table of serial numbers and allocated surgical implements in order to identify them. Depending on from which antenna the respective serial number has been received with which received power, the position of the respective surgical implement could be detected on the first display 9.

In this way, the position detection means 18 would be able to detect whether a particular surgical implement is actually located where it should be, which predetermined position is defined by the display of the true-to-life depiction of said surgical implement. For preparing the surgery, the surgical nurse would thus be able to place all surgical implements scheduled for the operation on the first display 9 at the predetermined positions and then press a key in order to obtain a clearance for surgery at the beginning of the surgical procedure. Thereupon, the device control 4 would actuate the position detection means 18 in order to check if all surgical implements illustrated in the display area 13 are actually located physically on the first display 9 at the predetermined positions. If one or several of those surgical implements is/are not located at all on the first display or is/are located on the first display 9 in an incorrect position, the device control 4 would depict an appropriate display information on the first display 9 or the second display 10. Thereupon, the surgical nurse could either correct her mistake or confirm that, in this specific case, a particular surgical implement is not necessary or should be located in a different position on the first display 9. This information would then be recorded also in the surgical protocol. In case all surgical implements are present on the first display 9, the device control 4 is, on the other hand, configured for indicating a clearance-for-surgery information on the first display 9 and/or the second display 10.

As a result, the advantage is obtained that, at the beginning of the surgical procedure, all surgical implements required for the operation are definitely located on the first display 9 at their positions as predetermined by the display of the true-to-life depiction of the surgical implements. And if not all surgical implements are located in their proper place, a reason for this is given in the surgical protocol along with the name of the person making the entry.

During the surgery, it is also recorded, in each case, when which surgical implement was taken from the first display 9 by the surgeon or the surgical nurse. At the end of the surgical procedure, it is also immediately obvious whether all surgical implements are again located on the first display 9. If, because of heavy soiling or a defect, a surgical implement is not to be placed on the first display 9 during the surgery, but is to be removed immediately, the menu navigation enables said surgical implement to be logged out. In the surgical protocol, this logging-out is again assigned to the person that has performed this action. As a result, surgical procedures can be made substantially more safe and comprehensible.

Furthermore, the device control 4 activates the display information indicated with the first display 9 and/or the second display 10 and/or the operating parameters as a function of the surgical implement which currently has been removed from the first display 9. For example, it is thus possible for the surgeon to remove the surgical handpiece 2 from the first display 9, which is detected by the position detection means 18 and notified to the device control 4. Thereupon, the device control 4 activates the pressure means 5 according to set values for this type of eye surgery and the respective position of the foot switch 3. The device control 5 thus changes operating parameters as a function of the surgical implement which, in each case, has been taken from the first display 9. If the surgeon puts the surgical handpiece 2 back on the first display 9, the device control 4 deactivates the pressure means 5. According to a different example, it would be possible for a special lamp for illuminating the environment of the eye to be activated when the surgeon takes the forceps 14 from the first display 9 in order to remove a foreign object from the patient's eye.

If the surgeon wishes to look up additional information prior to, during or after the surgery, he or she can actuate certain keys 17 on the first display 9 or the second display 10 in order to have said information indicated on the second display 10. In this way, the surgeon can, for example, leaf through the patient's file from the left to the right like through a book or retrieve additional information from a server or the internet and have it indicated on the second display. Similarly, it would be possible for a camera to be installed on the surgical handpiece 2 in order to display "live" an enlarged image of the eye in a display area 20 of the second display 10 during the surgery. Due to the surgeon's easy access to stored or currently recorded pieces of information, the surgeon is able to make substantially better decisions during the surgery.

Since the device 1 is designed in a very compact manner and its input means 7, apart from the foot switch 3, are formed only by the first display 9 and the second display 10, the device 1 can be hygienically cleaned particularly well. Wear of buttons or the danger of liquids penetrating from the surgical implements or from the gloves of the operating personnel into the casing 11 of the device 1 is also prevented advantageously by the choice of input means 7.

The surgical protocol established with the device 1 comprises not only the type of eye surgery which has been set, the chronology of all operating parameters adjusted or modified during the surgery and the patient data, but also the chronology as to when which surgical implement was located on the first display 9 or, respectively, when which surgical implement was removed from the first display 9. As a result, a surgical procedure can be retraced in a gapless manner in retrospect and the decisions of the surgeon can be examined.

Furthermore, it is advantageous that several operating parameters for certain types of eye surgery are already stored in the device 1 in a preset way and are adjusted automatically for the next operation by choosing the type of eye surgery.

Figure 3:
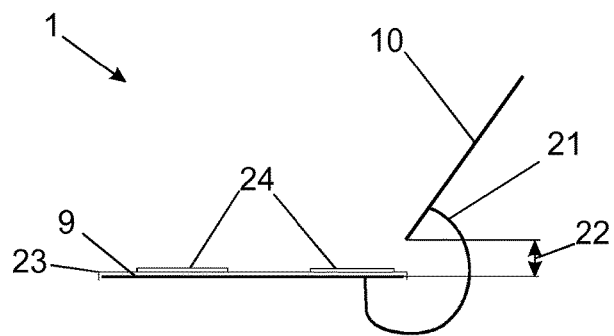
FIG. 3 shows a device for use in surgery in a diagrammed fashion from the side.

FIG. 3 shows a device 1 for use in surgery in a diagrammed fashion from the side. With this device 1, the second display 10 is fastened to the first display 9 by means of a mounting bracket 21. The mounting bracket 21 thereby undertakes the mechanical fastening, and the connecting cables for supplying the second display 10 run in the mounting bracket 21. Between the first display 9 and the second display 10, a gap 22 is provided which facilitates the cleaning of the displays 9 and 10 and allows a cover sheeting 23 to be placed over the first display 9 and optionally also over the second display 10. For sanitary reasons, the cover sheeting 23 can be replaced after each or after several operations.

It is particularly advantageous, however, that the cover sheeting 23 comprises several ribs 24. The ribs 24 are arranged so as to be essentially congruent with the surgical implements indicated on the first display 9 and constitute positioning means for positioning the surgical implements deposited on the first display 9. As a result, the surgical implements are prevented from rolling down inadvertently from the first display 9.

It may be mentioned that the second display 10, as illustrated in the figures, can, but does not have to be arranged behind the first display 9, as seen from the surgeon's point of view. For example, it would be possible to arrange the second display on one or both sides of the first display 9. In addition, the display 9 arranged at the back could then also be provided. The installation angle A can be defined from an only small tilt of, e.g., 5 degrees to a tilt of 90 degrees relative to the essentially horizontal first display.

It may be mentioned that "essentially horizontal" is to be understood such that surgical implements placed on the first display 9 shall not glide from the first display 9. Depending on the application, a slight inclination of the first display 9 is thus possible.

It may be mentioned that one or several sockets may be provided in the second display 10, for example, in the range of the display area 16, in order to electrically connect surgical implements to the device 1.

In the previous exemplary embodiments, the use of the device in eye surgery (cataract operations, vitrectomy operations, operations on the back of the eye) has been explained. However, the device can be adapted for the execution of other operations by adjusting the device control and the pieces of information indicated with the displays 9 and 10.

The invention claimed is:

1. A device for use in surgery to which a surgical implement is connectable in order to conduct surgery on a patient, wherein input means for controlling operating parameters and display means for indicating the operating parameters are provided, characterized in that the device comprises a first display which is horizontal during operation and a second display which runs obliquely upwards at an installation angle (A), wherein the device exhibits position detection means for detecting contactlessly communicating surgical implements deposited on the first display with regard to their positions on the first display, and wherein the device is configured for indicating true-to-life depictions of the individual surgical implements to be used for the respective eye surgery in a display area of the first display and that the position detection means are configured for notifying the presence or for notifying the absence of some or all of the depicted surgical implements to a device control.

2. The device according to claim 1, characterized in that the device is usable for the execution of eye surgery and that the surgical implement connectable to the device is formed by a surgical handpiece.

3. The device according to claim 1, wherein in the presence of all depicted surgical implements on the first display, the device control is configured for indicating a clearance-for-surgery information on the first display and/or the second display.

4. The device according to claim 1, wherein in the absence of at least one of the depicted surgical implements on the first display, the device control is configured for indicating a query information on the first display and/or the second display.

5. The device according to claim 1, wherein the device control is configured for establishing a surgical protocol in which, in addition to the operating parameters set in each case, it is recorded when which surgical implement was removed from the first display and was put back down on the first display.

6. The device according to claim 1, wherein the device control controls or changes, respectively, the display information indicated with the first display and/or the second display and/or the adjusted operating parameters of the device as a function of the surgical implement which currently has been removed from the first display.

7. The device according to claim 1, wherein that the first display and/or the second display constitutes input means and that, by actuating said input means, it is possible to leaf through the display information indicatable with the first display and/or the second display, in particular to the left and/or to the right.

8. The device according to claim 1, wherein the device comprises a foot switch for controlling individual operating parameters and that all further input means and/or all display means of the device are implemented by means of the first display and/or the second display.

9. The device according to claim 1, wherein with the input means, at least two different types of eye surgery are selectable, wherein the device control is configured for indicating various preset pieces of display information and for adjusting the operating parameters to predetermined operating parameters, depending on the respective choice of the type of eye surgery.

10. The device according to claim 1, wherein that the position detection means comprise an RFID reader which is configured for reading out contactlessly communicating RFID tags or RFID labels provided on the surgical implements in order to identify the surgical implements and to detect their positions on the first display.

11. The device according to claim 1, wherein a gap is provided between the first display and the second display.

* * * * *